United States Patent [19]
Mullers

[11] Patent Number: 5,133,763
[45] Date of Patent: Jul. 28, 1992

[54] JOINT PROSTHESIS

[76] Inventor: Jan B. Mullers, Oudegein 1, 3432 NC Nieuwegein, Netherlands

[21] Appl. No.: 449,953
[22] PCT Filed: Apr. 13, 1988
[86] PCT No.: PCT/NL88/00016
  § 371 Date: Dec. 27, 1989
  § 102(e) Date: Dec. 27, 1989
[87] PCT Pub. No.: WO88/07845
  PCT Pub. Date: Oct. 20, 1988

[30] Foreign Application Priority Data
  Apr. 14, 1987 [NL] Netherlands ............... 8700879

[51] Int. Cl.⁵ ............................................. A61F 2/34
[52] U.S. Cl. ................................................ 623/22
[58] Field of Search ............................. 623/22, 23

[56] References Cited
U.S. PATENT DOCUMENTS

| | | | |
|---|---|---|---|
| 4,241,463 | 12/1980 | Khovaylo | 623/23 |
| 4,623,352 | 11/1986 | Oh | 623/23 |
| 4,624,674 | 11/1986 | Pappas et al. | 623/22 |
| 4,770,658 | 9/1988 | Geremakis | 623/23 |
| 4,784,663 | 11/1988 | Kenna | 623/22 |
| 4,813,959 | 3/1989 | Cremascoli | 623/22 |

FOREIGN PATENT DOCUMENTS 3200340 9/1982 Fed. Rep. of Germany ........ 623/23

Primary Examiner—David Isabella
Attorney, Agent, or Firm—Edmund M. Jaskiewicz

[57] ABSTRACT

A joint prosthesis and a joint prosthesis organ comprising a cup-shaped element having two parts. One part (1) is a ring which may be connected to the cup-shaped second part (2) with use of click-joint elements (2',2") which are such that ring and cup-shaped part are allowed to rotate freely relative to each other. Described is that said ring may be formed such as to hamper luxation; the ring therefore may partially have an enlarged height. The surgeon using a joint prosthesis according to the invention on a patient has the possibility to rotate the ring with respect to the cup-shaped part until an optimal position is reached. If necessary the two parts may then be fixed to each other using separate means for fixation.

8 Claims, 5 Drawing Sheets

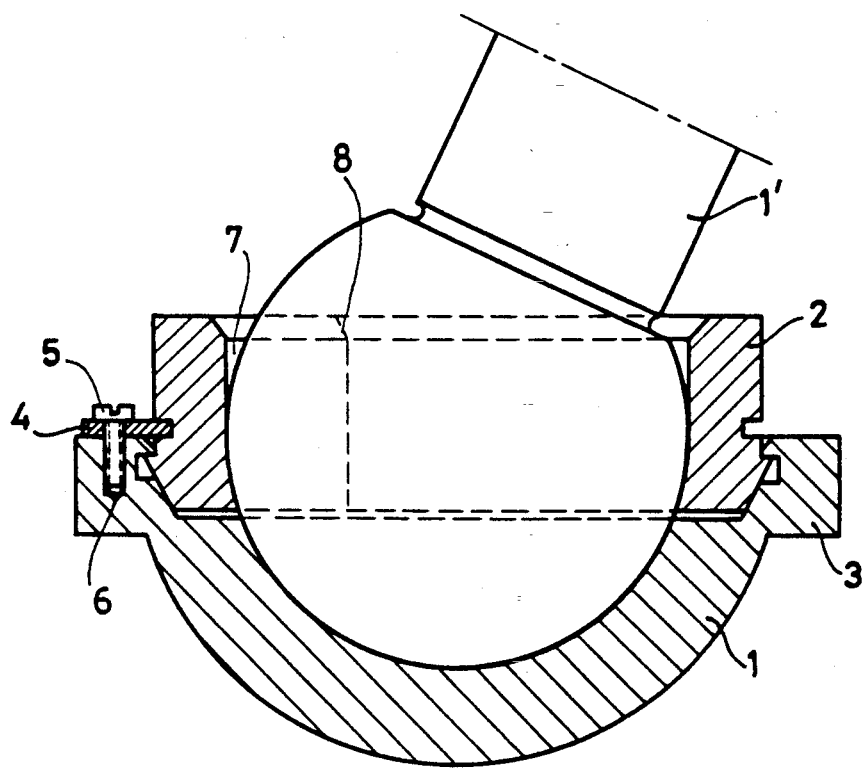
FIG:2a.
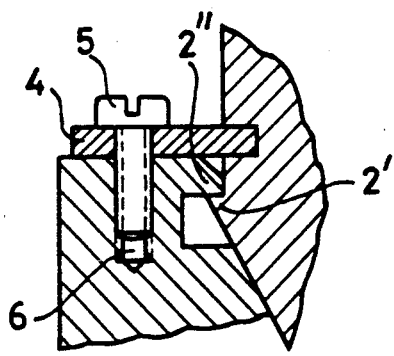
FIG:2b.

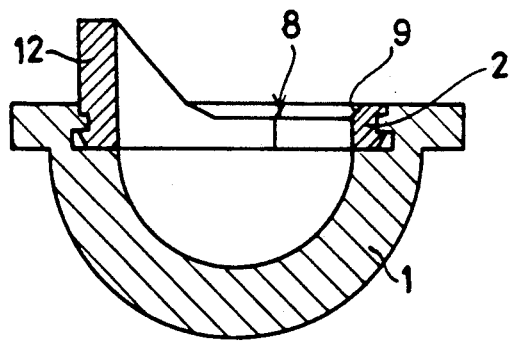
FIG: 3.
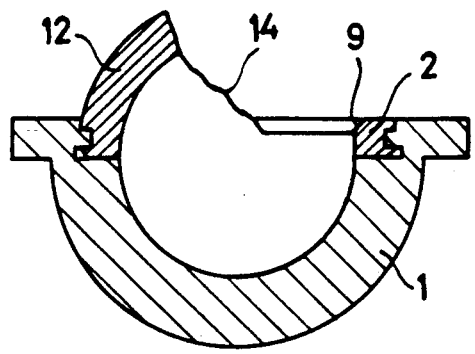
FIG: 4.
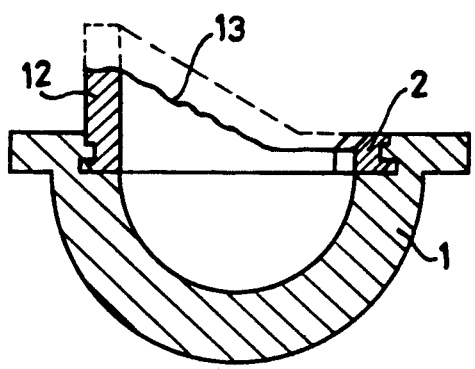
FIG: 5.

JOINT PROSTHESIS

FIELD OF THE INVENTION

The invention in the first place concerns a joint prosthesis, in particular a hip-joint prosthesis, at least consisting of an organ comprising a ball and an organ comprising a cup-shaped element for reception of said ball wherein the cup-shaped element at least consists of a first and a second part which are connected with each other and wherein the sphere-sector surface-shaped part of the contact surface between both parts of the cup-shaped element and the ball in the complete prosthesis equals to a solid angle of at most 180 degrees, of which the top coincides the heart of the ball.

BACKGROUND OF THE INVENTION

In the above given description of a joint-prosthesis is indicated that the applied ball may in no case be completely enclosed in the cup-shaped element. For that reason the sphere-sector surface-shaped part of the contact surface has been limited to at the most the surface of a half ball.

In the European patent application 0 053 794 a cup-shaped element is described, for use in a joint prosthesis as indicated above, whereby in the upper-inner edge of the cup-shaped element a recess is present for taking up a ring. The cup-shaped element is manufactured from a ceramic material while the ring is made of a plastic deformable material. The ring serves to protect both the ball and the cup of said prosthesis in case of occurrence of sub-luxation.

In some occasions however, depending on the condition of the patient, a certain hampering of luxation is necessary allthough luxation should remain possible in order to prevent damage to the bone material in which the cup is fixed using the usual cementing procedures or with mechanical means.

SUMMARY OF THE INVENTION

The present invention has as a goal to provide a joint prosthesis of the type described in which the cup-shaped element has such a form that luxation is prevented to a large extent, allthough principally luxation may still occur in cases of extreme mechanical load which otherwise would lead to damage of the bone parts to which the elements of such prosthesis are connected.

According to the invention the joint prosthesis, in particular a hip joint prosthesis is for that purpose characterized in that of the cup-shaped element said first part and said second part contain click-joint elements which can cooperate by forming a click-joint which allows free mutual rotation of both mentioned parts after connection thereof and wherein said second part consists of a ring of appropriate form which can be interchangeably connected with a recess in the inner-upper edge of the first part of said cup-shaped element while the inner side of the ring and the inner side of the first part of the cup-shaped element connect without difference of level and the height of the ring is greater than the depth of the recess over at least part of its circumference.

By applying click-joint elements to the second and first parts, which are shaped in such way that after connection of the first to the second part a mutual rotation of both parts is allowed, an optimal positioning of the second part within the first part can be achieved.

The application of the click-joint elements implies that it will have to be possible to elastically deform preferably at least one of the click-joint elements. For that reason at least one of the click-joint elements or that part of the organ of which the element is a part, will in general be made of synthetic material.

As the second part in the joint prosthesis of the organ containing a cup-shaped element is a part with a special form for prevention of luxation, the second part of the hip joint prosthesis can, after fitting of the complete hip joint prosthesis organ, be rotated in such way that in accordance with the on the spot established farthest positions an optimal position of the second part is reached. After this mentioned optimal position has been reached the second part can be further maintained in this position.

In particular seperately working means are provided for the mutual fixation of the said second part and first part after reaching an optimal position of the second part in regard to the first part. It is however noted that such seperately working means of fixation are not absolutely necessary; the friction against contortion of the second part in regard to the first may for instance be adjusted in such way that under normal conditions no contortion will occur and that contortion is only possible if the attending surgeon exercises a directed force.

In order to provide a higher friction between the first and the second part of the cup-shaped organ the contacting surfaces may be roughened.

Alternatively there may be a protrusion on one surface and a series of depressions in the opposite surface whereby upon rotation of the first and second parts relative to each other the said protrusion may be received by a selected one of said depressions.

A protrusion may have the form of a small ball received in an enclosing cavity in one of the contacting surfaces, for example in the first part of the cup-shaped organ, i.e. the cup-shaped element.

The invention also concerns a joint prosthesis organ comprising a cup-shaped element for application in a joint prosthesis according to the invention said cup-shaped element at least consisting of a first and a second part which can be connected with each other and in which the sphere-sector surface-shaped part of the contact surface between both parts of the cup-shaped element and the ball equals a solid angle of at the most 180 degrees, of which the top coincides with the heart of the ball which is characterized in that said first part and said second part comprise click-joint elements which can cooperate by forming a click-joint which allows free mutual rotation of both mentioned parts after connection thereof and wherein said second part consists of a ring of appropriate form which can be interchangeably connected with a recess in the inner-upper edge of said first part of said cup-shaped element whereby the inner side of the ring and the inner side of the first part of the cup-shaped element connect without difference of level and the height of the ring is greater than the depth of the recess over at least part of its circumference.

The first part and the second part in the joint prosthesis organ according to the invention form together a cup-shaped element wherein the second part is a ring of appropriate form which can, by means of a click-joint be interchangebly connected with a recess in the upper-inner edge of the first part element, with which the inner edge of the ring and the inner side of the cup-shaped element connect without difference of level and the height of the ring is at least equal to the depth of the recess. The ring is made of synthetic material, for instance high density polyethylene. The cup-shaped element can be made of synthetic material; certain metals or ceramic material can be used as well. The ring mentioned can be selected in such form and size that dependent on the patient's physical condition an optimal prevention of luxation can be achieved.

The first part of the joint prosthesis organ, is adapted to be fixed, in a known manner, in the bone structure of a patient with use of cementing or mechanical means.

As a result of the application of the above described construction form of the invention there is large accesibility upon fitting of the ball in the cup-shaped element; by applying the second part in the form of a ring the disengagement of the ball from the socket is impeded.

The above described ring-shaped second part may have different forms; for instance at least a part of its heightened circumference may be inclined towards the center of the cup-shaped element.

The earlier mentioned ring may also have been fit with a bevel in order to make a larger rotation angle of the ball fitting in the cup-shaped part possible.

In a most attractive construction form of the joint prosthesis organ according to the invention the second part of that organ is formed by a split ring.

A construction form such as this is most attractive in those cases in which the originally placed ring in a completely fitted joint prosthesis appears not to have a optimal form during the operation. The earlier fitted ring can then easily be removed and replaced by a new ring of a better adjusted form. Such a split ring may also be most advantageous in case of a subsequent operation of a patient; an earlier fitted ring which does not (any longer) have an optimal form can then easily be replaced by a new ring without the original fitted prosthesis having to be removed.

The invention also relates to a joint prosthesis organ comprising a cup-shaped element for application in a joint prosthesis said organ at least consisting of a first and a second part which can be connected with each other and in which the sphere-sector surface-shaped part of the contact surface between the cup-shaped element and the ball equals a solid angle of at the most 180 degrees, of which the top coincides with the heart of the ball which according to the invention is characterized in that said first part is formed by a plastics mass of such size that it can be adjusted as required to the bone area with which it is to be connected and in which a cavity has been made for reception by forming a click-joint, of said second part in the form of cup-shaped element whereby click-joint elements are present respectively at the upper edge of said cavity and at the outer-upper edge of said cup-shaped element.

For the application of the above described joint prosthesis organ the synthetic mass with a possible appropriate form is connected to or fitted in the pelvis; after this the cup-shaped element is fitted and the ball connected to the bone is placed after which finally by rotating the cup-shaped element in regard to the first part in the form of a synthetic mass an optimal positioning of the cup-shaped element is reached.

Finally the cup-shaped element may in turn be secured by means of seperate means in regard to the synthetic mass in which there is a hollow.

In the above described construction form the cup-shaped element may of course also be constructed in the manner as was described earlier; i.e. a cup-shaped element with in its inner-upper edge a recess in which a special ring can be included which is connected by means of a click-joint allowing free rotation of the ring in regard to the cup-shaped element.

If a joint prosthesis organ as described above is used then the first part having the form of a synthetic mass is of such size that it may be adapted during the operation, to the bone area to which the mentioned synthetic mass is to be connected; by in orthopaedics used means such a shaping can easily be performed during the operation.

In order to make it possible to check the fitting of the joint prosthesis inside a patient there will in general be seen to that at least the second part of the joint prosthesis organ that can be rotated in regard to the first part preceding the mutual fixation of both parts, will be visible in X-ray. A mark such as this may for instance be present on the second part in the form of a metal mark.

It is noted that click-joint elements which allow mutual rotation of the first and second part of the prosthesis organ can be completely circular while it may also be that the click-joint element on one of the parts is interrupted. The last construction has in particular the advantage that the force applied to the formation of the click-joint can be lesser in which way the possibility of damage to the prosthesis or to its place as well as damage to the concerned bone parts is reduced.

The invention will now be described with the aid of the accompanying drawing in which:

BRIEF DESCRIPTION OF THE DRAWINGS

FIG. 1 presents a section diagram of a joint prosthesis organ with a fitted ball according to the invention with which, as an exemplification, the part in which the click-joint elements are found is presented on a larger scale.

FIG. 3 presents yet another construction form of a joint prosthesis organ according to the invention.

FIG. 4 presents yet another construction form of a joint prosthesis organ according to the invention.

FIG. 5 presents an illustration of the application of a joint prosthesis organ according to the invention.

DESCRIPTION OF THE PREFERRED EMBODIMENT

Figure 2:
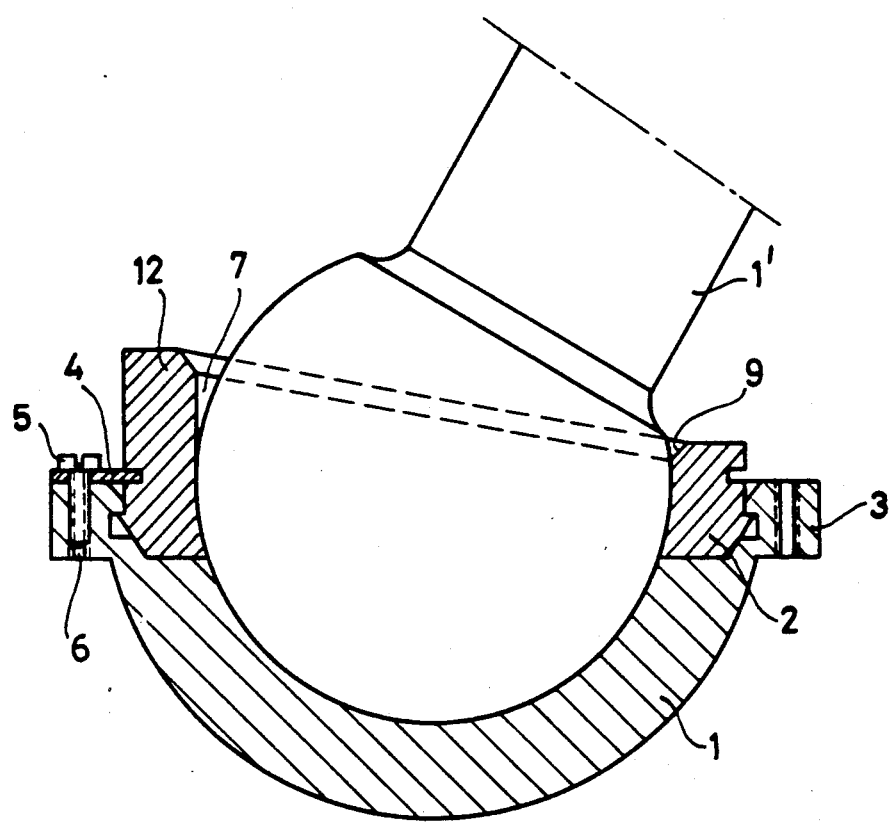
FIG. 2 presents a sectional drawing and an elevation of another construction form of a joint prosthesis organ according to the invention.

In FIG. 1 the first part is formed by a cup-shaped element 1 with a recess in the upper-inner edge in which a split ring 2 of synthetic material is incorporated of which the height is more than the depth of the recess. The height mentioned may, dependent on the eventual aim, be varied. Ring 2 is incorporated in the recess and is fitted or snapped together by means of elements 2' and 2'' which define a snap joint or click-joint and may have the form as presented here but which may also have any other suitable click-joint element form, as the expert knows, and which may both extend around the element 1 and ring 2 respectively, but of which one may also be interrupted as mentioned before. The cup-shaped part contains a flange 3 while it is furthermore indicated that fixation of the ring-shaped part 2 in regard to the cup-shaped part 1 can be achieved by fixation means 4 and 5 of which the screw 5 can be incorporated in hollow 6. The construction form of the prosthesis organ presented here is a basic construction form. The split of the ring at 8 makes it possible to fit the ring even if the prosthesis is completely finished; i.e. when the ball has been incorporated in the cup-shaped element.

Above indicated fixation can of course, as indicated afore, be accomplished without the use of special fixation means, i.e. by roughening of surfaces which contact each other. Also the earlier described protrusion and recesses in the contacting surfaces offer a good possibility.

When it is preferred to use separate fixation means they can also have the following form. The ring may have one or more notches in its outer circumference which extend over its height; by means of fasteners which fit in a notch and fall in recesses in the cups upper surface the ring can be fixed against rotation relative to the cup. The ring may also extend to over the cup edge. One or more notches may then be used to obtain fixation of the ring, by use of suitable fasteners, to a part normally used in uncemented prosthesis types, such as a metal ring which is screwed in the bone.

FIG. 2 presents a cup-shaped element 1 that is fitted with a ring-shaped part 2 with a heightened part 12 of which the height continuously increases from right to left. Furthermore the ring is provided with a bevel part 9 thus positively influencing the farthest positions of the ball-part of the joint. Such a ring of a special construction form, as well as the ring from FIG. 1 may be incorporated in the cup-shaped part 1, which is presented in FIG. 1. A patient may therefore at first be helped with a prosthesis according to FIG. 1; during the operation or maybe later, at a subsequent operation the part 2 can easily be replaced by a part as indicated in FIG. 2 and equally well by parts 2 as indicated in the figures that are still to be discussed.

FIG. 3 presents a ring-shaped second part of a special form while in FIG. 4 a similar prosthesis organ is presented with which the heightened part of the ring is inclined towards the center of the cup-shaped first part; in FIG. 4 is also indicated, at 14, that during the operation the ring-shaped part can be cut to the right size. It is noted that in FIG. 3 and 4 the heart of a ball that is to be fitted is fitted lower than in FIG. 1 and 2. A situation in which the heart of the ball lies in the plane of the upper side of the cup-shaped element 1 is of course also possible in the figures meant; which holds good for the following figures as well.

In FIG. 5 a construction form as in FIG. 3 is presented, with which it is schematically indicated that during the operation the heightened part 12 of the ring 2 can be given the right size by means of cutting as presented in 13.

Figure 6:
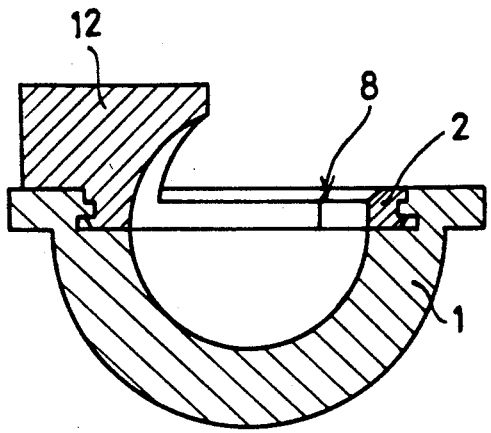
FIG. 6 presents a special construction form of a joint prosthesis organ according to the invention.

In FIG. 6 a situation is presented in which the ring 2 is constructed with a segment-shaped heightening 12 of limited size which extends only to a small part of the circumference. Such a ring is applied in case partial enclosure is necessary due to the most weak condition of the soft tissue.

In respect of afore given figures there is indicated that normally the inner edge of the ring and the inner side of the cup-shaped element connect without difference of level. However, in certain circumstances the ring may be adapted such that its inner surface displaced outward in respect of the inner surface of the cup at places of the ring which do not function to hamper luxation, i.e. generally at the right side of the figures.

Such displacement may be desirable to minimize the number of locations in which an overpressure of body fluids may occur.

Figure 7:
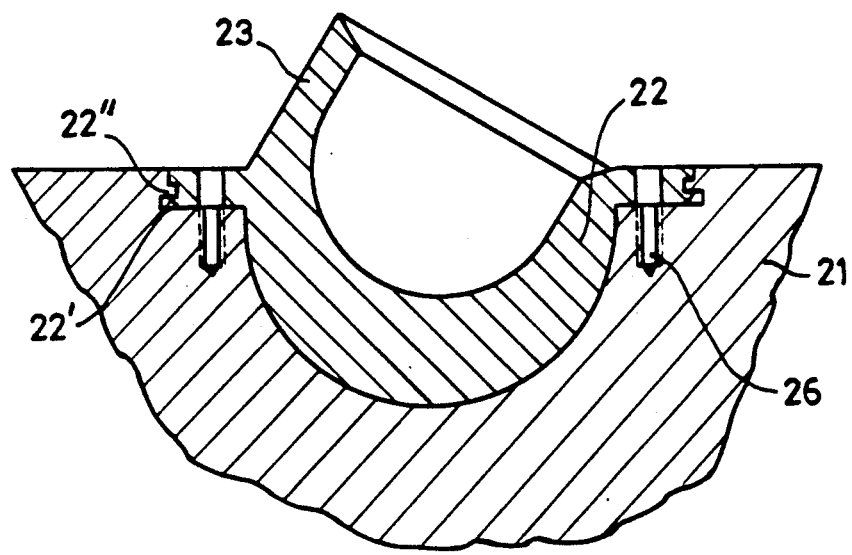
FIG. 7 presents a joint prosthesis organ according to the invention with which the second part is formed by a cup-shaped element.

In FIG. 7 a situation is presented in which the first part of the joint prosthesis organ consists of a synthetic mass 21, which, as is indicated, has been given a form which can be fitted in a hollow which is present in the pelvis-part while the second part 22 is constructed as a cup-shaped element. The cup-shaped element has in this case a form equal to that of FIG. 1; it is however fitted in a special manner. In order to fit such a joint prosthesis organ the synthetic mass 21 is first given the required size by means of cutting, sawing etc. After this part 21 is fitted, for instance by means of a cement, in a hollow which is present or made in the pelvis-part. After the fitting the cup-shaped element 22 is clicked into the hollow in the synthetic part; by rotating part 22 the correct position of the high side is adjusted after which the part 22 can be secured in regard to part 21 for instance by means of self-tapping screws. In that case the click-ring elements 22' and 22" are fitted in the inner side of the hollow in 21 and in the outer circumference side of the cup-shaped element 22 respectively. In the figures described above a number of constructions of a ring-shaped second part respectively a cup-shaped second part of a prosthesis organ have been presented.

The invention is however not restricted to the latter; the user will have a large number of construction forms at his disposal which can be applied according to choice.

Figure 8:
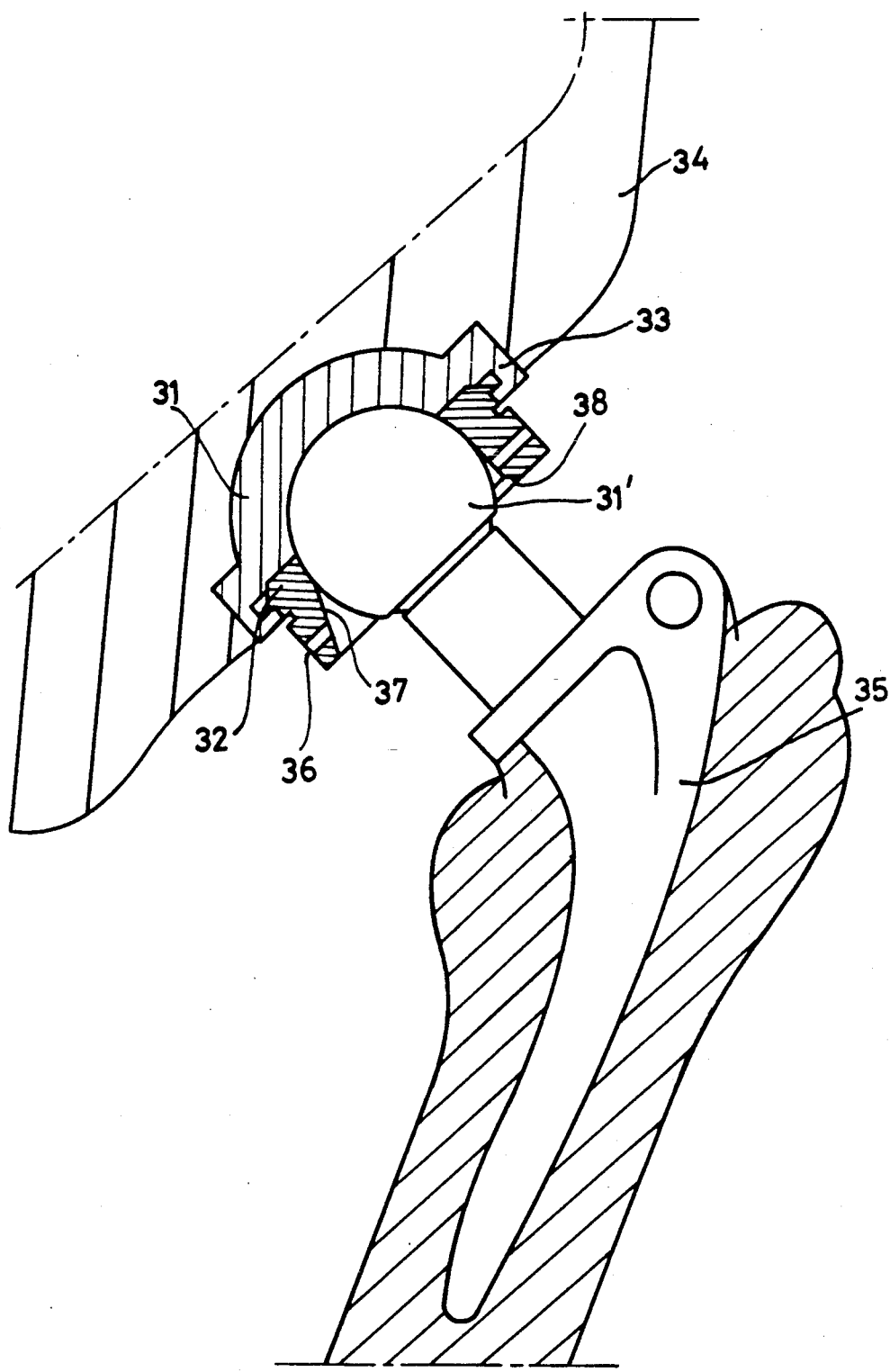
FIG. 8 presents a fitted joint prosthesis organ according to the invention.

Finally in FIG. 8 a diagrammatic representation is given of a fitted hip-joint prosthesis according to the invention. In the pelvis 34 a cup-shaped element 31 has been fitted in the known manner; the ball 31' has been incorporated. Connected with the ball is the pin 35 which is incorporated in the thigh-bone. Indicated here is a ring-shaped part 32, which is incorporated in a recess in the cup-shaped part 31; the ring-shaped part is here indicated with a strong bevel at 37 and light bevel at 38. The light bevel is present in the area where the danger of luxation is greatest.

It is furthermore indicated at 36 that perforations have been made in the ring in order to stimulate ingrowth of soft tissue in which way an extra strong connection of the entire prosthesis is achieved. Perforations can be made in all of the above drawn constructions; the application of an asymetric bevel pattern as drawn can be made with all construction forms as well.

I claim:

1. In a joint prosthesis for a hip joint, a cup-shaped element adapted to be secured in the pelvis, said cup-shaped element comprising a first part having a concave spherical surface opening of not more than 180°, said opening being surrounded by a rim and adapted to receive a joint ball therein, and said rim defining an inner edge and having an annular recess formed therein; and an annular second part defining an inner surface, said inner surface, when said second part is seated in said annular recess, being substantially/co-extensive and flush with said spherical surface to define a contact surface not greater than 180°, said annular second part having a height which is over at least a part of its circumference greater than the depth of said recess, and means comprising a snap joint between said first and second parts for rotatably retaining said second part in said recess of said first part.

2. In a joint prosthesis as claimed in claim 1 and further comprising further means on said first part of said cup-shaped element and engageable with means defining a notch on said annular second part for securing said first and second parts together.

3. In a joint prosthesis for a hip joint comprising a first element comprising a ball and a second element comprising a cup-shaped element adapted to be secured in the pelvis to receive said ball element therein so as to define therewith a ball and socket joint, said cup-shaped element comprising a first part having a concave spherical surface opening of not more than 180 degrees, said opening being surrounded by a rim and adapted to receive a a joint ball therein, said rim defining an inner edge and having an annular recess formed therein; and an annular second part defining an inner surface, said inner surface, when said second part is seated in said annular recess, being substantially/co-extensive and flush with said spherical surface to define a contact surface not greater than 180 degrees, said annular part having a height which over at least a part of its circumference is greater than the depth of said recess, and means comprising a snap joint between said first and second parts for rotatably retaining said second part in said recess of said first part.

4. In a joint prosthesis as claimed in claim 1 wherein said annular second part has a first end seated in said annular recess and a second end directed away from said first part, there being a bevel around at least a portion of the inner edge of said second end.

5. In a joint prosthesis as claimed in claim 1 wherein said second part comprises a split ring.

6. In a joint prosthesis as claim in claim 1 wherein said height of said annular second part defines a minimum height thereof.

7. In a joint prosthesis as claimed in claim 6 wherein said minimum height extends over a portion of the circumference of said annular second part and the remaining portion of said circumference has a height greater than said minimum height.

8. In a joint prosthesis as claimed in claim 7 wherein the height of said annular second part varies uniformly from said minimum height to a height greater than the minimum height.

* * * * *